United States Patent [19]

Bennet

[11] Patent Number: Plant 5,274

[45] Date of Patent: Aug. 28, 1984

[54] MINIATURE ROSE PLANT 'ROSY DAWN'

[76] Inventor: Cecelia L. D. Bennet, 489 Minot Ave., Chula Vista, Calif. 92010

[21] Appl. No.: 464,031

[22] Filed: Feb. 4, 1983

[51] Int. Cl.[3] ..... A01H 5/00

[52] U.S. Cl. ..... Plt./7

[58] Field of Search ..... Plt./7

*Primary Examiner*—James R. Feyrer

[57] ABSTRACT

The subject of the present disclosure is a new and distinct variety of miniature rose plant characterized by it's rich yellow edged in red bloom.

1 Drawing Figure

1

The present invention relates to a new variety of hardy, dwarf, miniature rose plant of the miniature class; the variety being primarily characterized as a yellow blend.

The variety is further characterized by:

Long stemmed show type one to a stem blooms.

A slight tea fragrance.

The plant ranges in height from 12 to 24 inches. The branches are sturdy and erect, much branched with medium foliage covering. A very heavy bloomer. Grows well in the hothouse as well as outdoors.

The present variety of miniature rose plant was originated by me at Tiny Petal's Nursery, located at Chula Vista, Calif., under careful observation, and is a self of "Magic Carrousel" U.S. Plant Pat. No. 3,601 introduced by Sequoia Nursery in 1972.

Subsequent to the origination of the variety I successfully reproduced it at Tiny Petal's Nursery located at aforesaid with reproductions coming true in all respects. I have found the plant to be easily asexually reproduced from cuttings.

The color photographs illustrate the variety.

Referring now specifically to the new and distinct variety of miniature rose plant, the following is a detailed description thereof in outline; all major color plate identification being in reference to the British Colour Council Horticultural Chart.

Type: Dwarf; compact; seedling; greenhouse; outdoors; cut flowers; garden decoration; potted plant.

Class: Miniature.

Variety name: "Rosy Dawn".

Flowers: One to a stem.

Quantity of bloom: Very prolific.

Bud:

*Peduncle.*—Long, slender, reddish, 1 to 1½ inches in length.

*Hairs.*—Very minute, reddish.

*Before calyx breaks.*—Size small. Form ovoid, sepals extending well out over the end of the bud. Color medium green with reddish tinge.

*As calyx breaks.*—Color reddish. Opens well in all weather.

Bloom: Size when fully open averaging from 1½ to 1¾ inches in diameter. Petalage double averaging from 25 to 30 petals, arranged regularly.

*Form.*—Center petals slightly smaller than outer petals. Opens slowly with gentle reflexing of the outer edge of the petals. Open flower reveals a generous amount of stamens.

2

Petals: Good substance, matt surface topside and underside of petals.

*Shape.*—Outer petals lanceolate with minute tip.

*Intermediate petals.*—Broad lanceolate with minute tip.

*Inner petals.*—Slightly elongated accompanied by a few petaloids.

Color: Newly opened flowers as grown by me at Chula Vista, Calif.

Outer petals: Topside surface, lower part of the petal barium yellow 503/1, page 131, with the outer edge of the petal geranium lake 20/1, page 20.

Outer petals: Underside of petal surface, barium yellow 503/2, page 131, with narrow tinge of geranium lake 20/1, page 20, on the outer edge.

Intermediate petals: Topside surface, barium yellow 503/1, page 131, on lower part of petal with geranium lake 20/1, page 20, on outer edge.

Intermediate petals: Underside of petal surface, barium yellow 503/2, page 131, with narrow tinge of geranium lake 20/1, page 20, on the outer edge.

Center petals: Topside surface, barium yellow 503/1, page 131, with geranium lake 20/1, page 20, on outer edge of the petal.

Center petals: Underside of petal surface, barium yellow 503/2, page 131, with narrow tinge of geranium lake 20/1, page 20, on the outer edge.

Behavior: Opens well in all weather. Opens slowly. Fast repeat blooming cycle. The bloom has excellent lasting qualities.

Reproductive organs:

*Stamens.*—A generous amount arranged evenly around pistil.

*Filament.*—Varying lengths.

*Pollen.*—Abundant.

*Pistil.*—Short, abundant and spreading.

*Styles.*—Short and irregular.

*Overies.*—All encased in calyx.

*Hips.*—Yes.

*Seeds.*—Yes.

Foliage:

*Leaves.*—Compact of five to seven, medium sized.

*Leaflets.*—Shape, broad, arrow shaped.

*Margin.*—Very serrated with a reddish tinge on edge.

*Color.*—Medium green.

Rachis: Medium length, underside smooth.

*Stipule.*—Medium length, medium width, reddish.

Growth:

*Habit.*—Bushy, much branched.

*Growth.*—Vigorous.

*Canes.*—Long, straight, strong.
*Main stem.*—Color medium green.
*Thorns.*—Small, slender, reddish.
*Prickles.*—None.
*Branches.*—Color medium green with a reddish tinge.

The miniature rose plant and its flowers as herein described may vary in slight detail due to climatic, soil and cultural conditions under which the variety may be grown. The present description being of the variety as grown by me at Chula Vista, Calif.

I claim:

1. A new and distinct variety of miniature rose plant of hardy, dwarf, bushy, much branched habit, substantially as illustrated and described, characterized by bud and flowers.

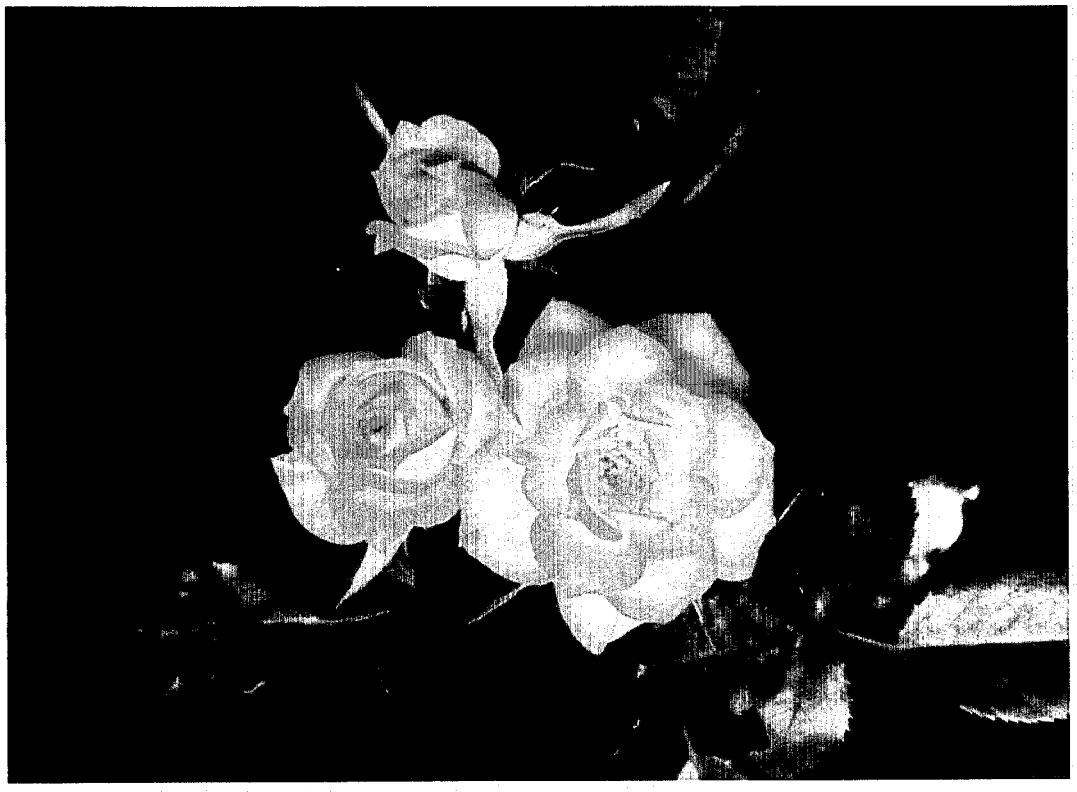

* * * * *